US012326408B2

(12) United States Patent
Zeng et al.

(10) Patent No.: US 12,326,408 B2
(45) Date of Patent: Jun. 10, 2025

(54) DETECTION METHOD, APPARATUS AND SYSTEM (71) Applicants: Nuctech Company Limited, Beijing (CN); Tsinghua University, Beijing (CN)

(72) Inventors: Zhi Zeng, Beijing (CN); Jianmin Li, Beijing (CN); Ming Ruan, Beijing (CN); Yanli Deng, Beijing (CN); Guoping Zhu, Beijing (CN); Junli Li, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 156 days.

(21) Appl. No.: 18/266,507

(22) PCT Filed: Nov. 25, 2021

(86) PCT No.: PCT/CN2021/133067
§ 371 (c)(1),
(2) Date: Jun. 9, 2023

(87) PCT Pub. No.: WO2022/121691
PCT Pub. Date: Jun. 16, 2022

(65) Prior Publication Data
US 2024/0027371 A1    Jan. 25, 2024

(30) Foreign Application Priority Data
Dec. 10, 2020  (CN) .......................... 202011437355.9

(51) Int. Cl.
*G01N 23/10*   (2018.01)
*G01N 23/20025*   (2018.01)

(52) U.S. Cl.
CPC ....... *G01N 23/10* (2013.01); *G01N 23/20025* (2013.01); *G01N 2223/3307* (2013.01); *G01N 2223/643* (2013.01)

(58) Field of Classification Search
None
See application file for complete search history.

(56) References Cited

U.S. PATENT DOCUMENTS

2008/0315091 A1* 12/2008 Morris .................... G01V 5/222
  250/306
2011/0248163 A1* 10/2011 Morris ................. G01N 23/046
  250/306

(Continued)

FOREIGN PATENT DOCUMENTS

CN   103308938 A   9/2013
CN   102203637 B   5/2015

(Continued)

OTHER PUBLICATIONS

International Search Report dated Feb. 28, 2022 issued for International PCT Application No. PCT/CN2021/133067.

(Continued)

*Primary Examiner* — Hoon K Song
(74) *Attorney, Agent, or Firm* — K&L Gates LLP (57) ABSTRACT Embodiments of the present application provide a detection method. The detection method includes: acquiring information of at least two first positions through which a particle passes before penetrating an object under detection, and information of at least two second positions through which the particle passes after penetrating the object under detection, wherein the object under detection is a metal product; reconstructing, based on the information of the at least two first positions, a first track before the particle penetrates the object under detection; reconstructing, based on the information of the at least two second positions, a second track (Continued)

after the particle penetrates the object under detection; processing the first track and the second track to obtain feature information of the object under detection; and determining, according to the feature information and preset feature information of an object of a target type, a detection result of the object under detection.

9 Claims, 4 Drawing Sheets

(56) References Cited

U.S. PATENT DOCUMENTS

| | | | |
|---|---|---|---|
| 2015/0212014 A1* | 7/2015 | Sossong | G01V 5/22 250/394 |
| 2015/0245802 A1* | 9/2015 | Sossong | A61B 6/4092 600/407 |
| 2016/0041297 A1 | 2/2016 | Blanpied et al. | |
| 2016/0104290 A1* | 4/2016 | Patnaik | G06F 18/24 382/173 |
| 2016/0260578 A1* | 9/2016 | Sossong | G01V 5/22 |
| 2017/0357026 A1 | 12/2017 | Gallagher et al. | |

FOREIGN PATENT DOCUMENTS

| | | |
|---|---|---|
| CN | 105549103 A | 5/2016 |
| CN | 105700029 A | 6/2016 |
| CN | 105074440 B | 5/2018 |
| CN | 105393111 B | 7/2018 |
| CN | 109283588 A | 1/2019 |
| CN | 106233160 B | 2/2019 |

OTHER PUBLICATIONS

Gary Blanpied, et al., "Material discrimination using scattering and stopping of cosmic ray muons and electrons: Differentiating heavier from ligher metals as well as low-atomic weight materials", Nuclear Instruments and Methods in Physics Research Section A., vol. 784, Jun. 1, 20215, p. 352-358.

Zheng Yifan, et al., "Discrimination of drugs and explosive in cargo inspections by applying machine learning in muon tomography", Nuclear Instruments and Methods in Physics Research Section A, vol. 30, No. 8, Aug. 31, 2018.

Feng Hanliang, et al., Review of Muon Tomography, Nuclear Electronics & Detection Technology, Aug. 2010, vol. 30, No. 8.

EPO; Extended European Search Report for European Patent Application No. 21902398.3 dated Dec. 4, 2024, 8 pages.

Bozhko, N.I., et al., "Cosmic-Ray Muon Tomography Setup: Long-Term Life of Drift Tube Chambers", Elementary Particles and Fields Experiment, ISSN 1063-7788, Physics of Atomic Nuclei, 2020, vol. 83, No. 2, pp. 258-261.

* cited by examiner

DETECTION METHOD, APPARATUS AND SYSTEM

CROSS-REFERENCE TO RELATED APPLICATIONS

The present application is a National Stage of International Application No. PCT/CN2021/133067, filed on Nov. 25, 2021, which claims the priority to Chinese Patent Application No. 202011437355.9 filed on Dec. 10, 2020, both of which are incorporated herein by reference in their entireties.

TECHNICAL FIELD

The present application relates to the technical field of security inspection, and particularly, to a detection method, apparatus and system.

BACKGROUND

An elemental substance is a pure substance composed of the same element. Many products made of the elemental substance, especially noble metal products made of the elemental substance, may be used as currency, and may be reserved and mortgaged, so they are often subject to counterfeiting.

Currently, the proportional analysis method is typically used to detect the authenticity of the product made of the elemental substance (collectively referred to as an object under detection herein). For example, the authenticity of the object under detection may be determined according to the density of the object under detection. However, since many counterfeit products made of the elemental substance are made to have the same density as the authentic products made of the elemental substance, and the surface is coated with a layer made of the elemental substance, the proportional analysis method cannot detect the authenticity of the object under detection, reducing the accuracy of the detection result. Therefore, there is an urgent need for a high accuracy detection method.

SUMMARY

Embodiments of the present application provide a detection method, apparatus and system.

In a first aspect, the embodiments of the present application provide a detection method, including: acquiring information of at least two first positions through which a particle passes before penetrating an object under detection, and information of at least two second positions through which the particle passes after penetrating the object under detection, wherein the object under detection is a metal product; reconstructing, based on the information of the at least two first positions, a first track before the particle penetrates the object under detection; reconstructing, based on the information of the at least two second positions, a second track after the particle penetrates the object under detection; processing the first track and the second track to obtain feature information of the object under detection; and determining, according to the feature information and preset feature information of an object of a target type, a detection result of the object under detection.

In a second aspect, the embodiments of the present application further provide a detection apparatus, including: an acquisition module, configured to acquire information of at least two first positions through which a particle passes before penetrating an object under detection, and information of at least two second positions through which the particle passes after penetrating the object under detection, wherein the object under detection is a metal product; a first reconstruction module, configured to reconstruct, based on the information of the at least two first positions, a first track before the particle penetrates the object under detection; a second reconstruction module, configured to reconstruct, based on the information of the at least two second positions, a second track after the particle penetrates the object under detection; a processing module, configured to process the first track and the second track to obtain feature information of the object under detection; and a detection module, configured to determine, according to the feature information and preset feature information of an object of a target type, a detection result of the object under detection.

In a third aspect, the embodiments of the present application further provide a detection system, including: a first detector, configured to detect information of at least two first positions through which a particle passes before penetrating an object under detection; a second detector, configured to detect information of at least two second positions through which the particle passes after penetrating the object under detection; a carrying unit, configured to carry the object under detection; and a detection unit, configured to perform any method according to the first aspect.

BRIEF DESCRIPTION OF THE DRAWINGS

In order to illustrate technical solutions of embodiments of the present application more clearly, the drawings required for the embodiments of the present application will be briefly described. For a person skilled in the art, other drawings can also be obtained from these drawings without any inventive effort.

DETAILED DESCRIPTION

Features and exemplary embodiments of various aspects of the present application will be described in detail below. In order to make the objects, technical solutions and advantages of the present application clearer, the present application is further described in detail below with reference to the drawings and specific embodiments. It should be understood that, specific embodiments described herein are merely for the illustration of the present application, not for limiting the present application. For those skilled in the art, the present application may be implemented without some of these specific details. The following description of the embodiments is only for providing a better understanding of the present application by illustrating examples of the present application.

It should be noted that, relational terms such as "first" and "second" herein are used only for distinguishing one entity or operation from another entity or operation, and do not necessarily require or imply any such actual relationship or order between these entities or operations. Moreover, the terms "comprising", "including", or any other variation thereof, are intended to encompass a non-exclusive inclusion, such that a process, a method, an article or a device including a series of elements not only includes these elements, but also includes other elements not explicitly listed, or includes elements inherent to the process, the method, the article or the device. Without further limitation, an element preceded by "including . . . " does not exclude presence of additional similar elements in a process, a method, an article or a device including the element.

Based on the BACKGROUND, it is known that many products made of the elemental substance are often subject to counterfeiting. Especially, noble metal products (such as, gold) made of an elemental substance are often subject to counterfeiting and fraud since the noble metal products may be used as currency, and may be reserved and mortgaged.

However, for counterfeit products that are made to have the same density as the authentic products made of the elemental substance and that are only coated with a layer made of the elemental substance on the surface, it is impossible to detect their authenticity by using the conventional proportional analysis method. For example, counterfeit gold brick products may typically be made with tungsten powder to have the same density as gold, and then are coated with a layer made of gold on the surface.

A large part of components of natural cosmic rays are charged muons, which are also called muons with high-energy. Basic properties of muons are similar to basic properties of electrons, but the mass of the muons is about 200 times of the mass of the electrons. Under a condition that the muons penetrate an object under detection, the muons scatter many times at small angles with nuclei of the object under detection. Materials with different atomic numbers, that is, materials of different types, have different scattering angles, and a distribution of the scattering angles is different. By extracting feature information including the scattering angles of the object under detection and the distribution of the scattering angles, characteristics of a material of the object under detection can be detected.

About 200 muons fall on one square meter of the earth's surface per second on average. When the muons penetrate through the object under detection, interactions including ionization and nuclear reaction occur, and a part of the energy is lost. Information of positions about where the muons are positioned on detectors can be detected by using the detectors such as a drift tube, a scintillation crystal bar, or a position sensitive detector, etc. By reconstructing tracks of the muons, the muons may be counted and the energy of the muons may be measured.

Furthermore, interactions between muons and nuclei with a high atomic number are strong, and the interactions may be used to detect matters with heavier nuclide, so that the muon imaging technology may be used to detect the elemental substance (such as, the noble metal product) and a special nuclear material.

Accordingly, based on the above findings of the inventors, in order to solve the problems existing in the prior art, embodiments of the present application provide a detection method, apparatus and system, so that a detection result of the object under detection may be determined based on tracks before and after the particle penetrates the object under detection, so as to prevent a false detection due to a similarity in a density between objects under detection, thereby improving accuracy of the detection result.

Figure 1:
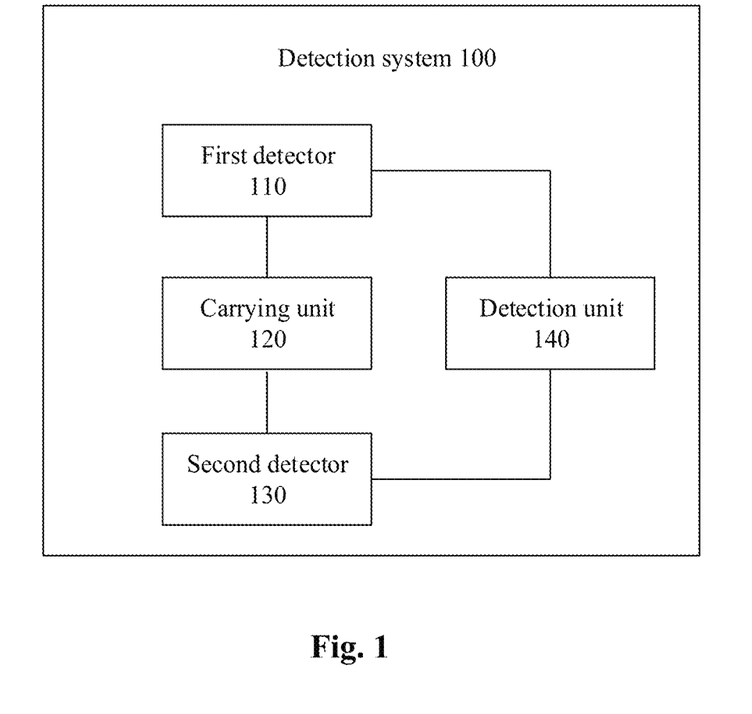
FIG. 1 is a schematic structural view of a detection system according to an embodiment of the present application.

A subject performing the detection method according to the embodiments of the present application may be a detection system, and as shown in FIG. 1, the detection system 100 may include: a first detector 110, which may be configured to detect information of at least two first positions through which a particle passes before penetrating an object under detection; a second detector 130, which may be configured to detect information of at least two second positions through which the particle passes after penetrating the object under detection; a carrying unit 120, which may be configured to carry the object under detection; a detection unit 140, which may be configured to perform the detection method according to the embodiments of the present application. The detection method will be described in detail in an embodiment of the detection method shown in FIG. 3, which will not be repeated here for simplicity.

The object under detection is any metal product under detection. For example, the object under detection may be an elemental product with a high atomic number, a noble metal product, and the like. The object under detection may be detected in a bare manner or in a package.

The information of the first position is points on the track on the detector before the particle penetrates the object under detection. The information of the second position is points on the track on the detector after the particle penetrates the object under detection. The points on the track may be specific coordinates.

In some embodiments, the first detector 110 may be arranged at one side of the carrying unit 120, and the first detector 110 may include at least two detectors.

The second detector 130 may be arranged at the other side of the carrying unit 120, and the second detector 130 may include at least two detectors.

In some embodiments, the particle may include at least one of a muon and an electron.

The electron may be an electron with high-energy, that is, an electron with energy greater than a preset energy value, and the preset energy value may be set according to actual requirements. Accordingly, a situation is avoided in which the detection fails under a condition that energy is totally absorbed by the object under detection when an electron with low energy irradiates the object under detection.

Different particles may be used to detect different objects under detection with different thicknesses. For example, the muon or the electron may be used to detect a relatively thin object under detection. Since an electron does not have enough energy to penetrate a relatively thick object under detection, the muon may be used to detect the relatively thick object under detection.

In some embodiments, the detectors may include at least one of a drift tube, a scintillation crystal bar, and a position sensitive detector. The drift tube may be a gas drift tube.

In some embodiments, the carrying unit 120 may include at least one of a tray or a conveyor. Whether the object under detection is in a stationary state or a moving state, the carrying unit 120 according to the embodiment of the present application may achieve the detection of the object under detection, so that applicability of the detection system can be improved.

Figure 2:
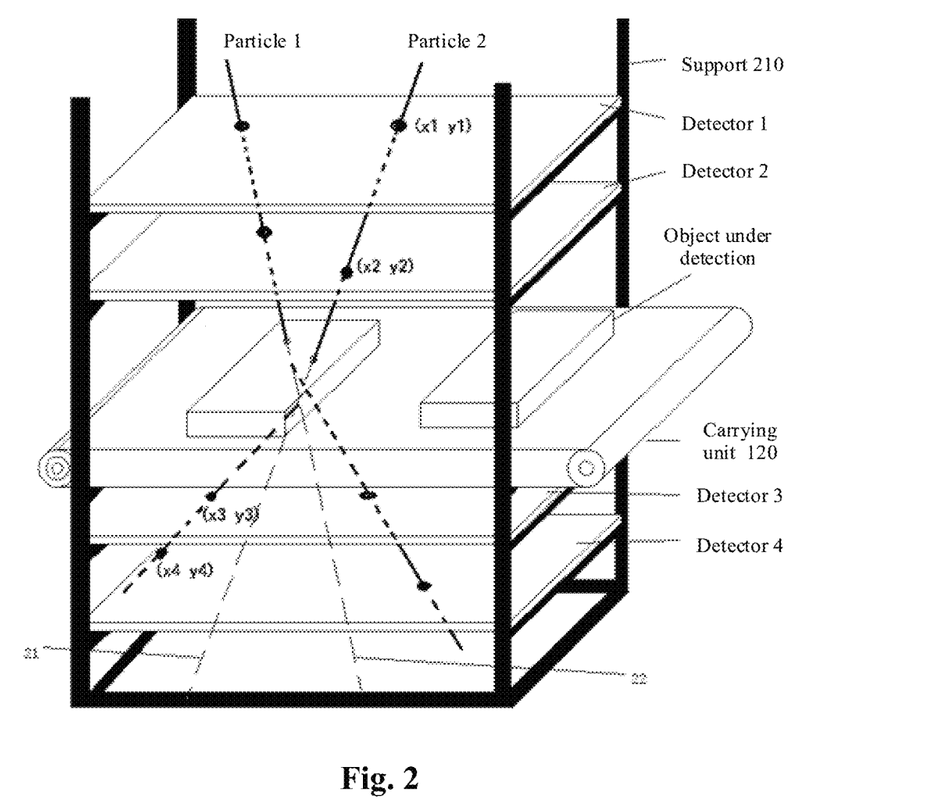
FIG. 2 is a schematic structural view of a detection system according to an embodiment of the present application.

Specifically, with reference to FIG. 2, the first detector 110 and the second detector 130 each include two detectors. FIG. 2 is a schematic structural view of a detection system according to an embodiment of the present application.

As shown in FIG. 2, a detector 1 and a detector 2 constitute the first detector 110, and are both arranged at one side of the carrying unit 120. A detector 3 and a detector 4 constitute the second detector 130, and are both arranged at the other side of the carrying unit 120. The detector 1, the detector 2, the detector 3, the detector 4 and the carrying unit 120 are arranged on a support 210. In FIG. 2, (x1, y1) represents information a first position of a particle 2 on the detector 1, (x2, y2) represents information of the first position of the particle 2 on the detector 2, (x3, y3) represents information of a second position of the particle 2 on the detector 3, (x4, y4) represents information of a second position of the particle 2 on the detector 4, and a dashed line 21 represents a partial track of the particle 2 under a condition that the particle 2 does not penetrate the object under detection.

The support 210 may be made of iron or a lightweight metal material, and a periphery of the support 210 may be covered with a lightweight thin plate material, for example, the periphery of the support 210 may be covered with an aluminum plate.

It is understood that a particle 1 and the particle 2 in FIG. 2 are merely illustrative, and, in actual practice, more or fewer particles may be used according to the actual requirements. In FIG. 2, points (whose coordinates are not shown) on each detector are points on a track of the particle 1 on the detector 1, the detector 2, the detector 3 and the detector 4, and a dashed line 22 represents a partial track of the particle 1 under a condition that the particle 1 does not penetrate the object under detection. A vertical coordinate of information of each position is a height of a detector where the coordinate is positioned.

The detection system 100 may be used to perform the detection method shown in FIG. 3 below, specific principles and effects thereof may be referred to the detailed description of FIG. 3 and will not be repeated here for simplicity.

The detection method according to the embodiment of the present application is described below.

Figure 3:
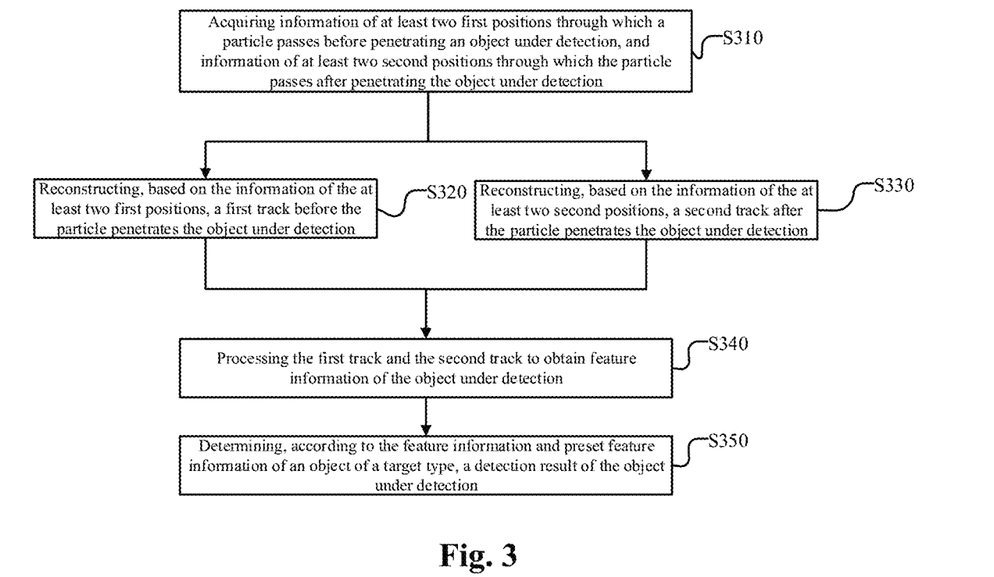
FIG. 3 is a schematic flowchart of a detection method according to an embodiment of the present application.

FIG. 3 shows a schematic flowchart of a detection method according to an embodiment of the present application. As shown in FIG. 3, the method may include step 310, step 320, step 330, step 340, and step 350.

Step 310: acquiring information of at least two first positions through which a particle passes before penetrating an object under detection, and information of at least two second positions through which the particle passes after penetrating the object under detection.

The object under detection may be a metal product.

The particle may include at least one of a muon and an electron. Similarly, the electron may be an electron with high-energy, that is, an electron with energy greater than a preset energy value, and the preset energy value may be set according to actual requirements. Different particles may be used to detect different objects under detection with different thicknesses.

In the embodiment of the present application, when the object under detection is detected, the object under detection may be placed on the carrying unit, and the particle is used to irradiate the object under detection. The first detector arranged at one side of the carrying unit may detect the information of the at least two first positions through which the particle passes before penetrating the object under detection, and the second detector arranged at the other side of the carrying unit may detect the information of the at least two second positions through which the particle passes after penetrating the object under detection.

Step 320: reconstructing, based on the information of the at least two first positions, a first track before the particle penetrates the object under detection.

The first track is a track reconstructed, based on the information of the at least two first positions, before the particle penetrates the object under detection.

In the embodiment of the present application, after the information of the at least two first positions through which the particle passes before penetrating the object under detection is acquired, the first track before the particle penetrates the object under detection may be reconstructed based on the information of the at least two first positions. For example, the first track may be constructed by fitting or connecting the acquired information of each first position.

Step 330: reconstructing, based on the information of the at least two second positions, a second track before the particle penetrates the object under detection.

The second track is a track reconstructed, based on the information of the at least two second positions, after the particle penetrates the object under detection.

In the embodiment of the present application, after the information of the at least two second positions through which the particle passes before penetrating the object under detection is acquired, the second track after the particle penetrates the object under detection may be reconstructed based on the information of the at least two second positions. For example, the second track may be constructed by connecting the acquired information of each second position.

It is understood that the step 320 and the step 330 may be performed at the same time, or in sequence without distinguishing of sequential order.

Step 340: processing the first track and the second track to obtain feature information of the object under detection.

In the embodiment of the present application, after the first track and the second track are reconstructed, the first track and the second track may be processed to obtain the feature information of the object under detection. The feature information may include at least one of a scattering angle and a distribution of the scattering angle, or the feature information may include at least one of a scattering force and a blocking force.

Specifically, for example, a scattering angle of the first track may be calculated and a distribution of the scattering angle of the first track may be analyzed, and a scattering angle of the second track may be calculated and a distribution of the scattering angle of the second track may be analyzed, and accordingly, feature information under this condition may be at least one of the scattering angle and the distribution of the scattering angle. Alternatively, a force (which may be the scattering force or the blocking force for example) of the object under detection on the particle may be calculated according to the first track and the second track, and accordingly, the feature information may be at least one of the scattering force and the blocking force.

Step 350: determining, according to the feature information and preset feature information of an object of a target type, a detection result of the object under detection.

The object of the target type is a possible product made of an elemental substance of a preset object under detection, such as a product made of gold or silver.

The preset feature information is feature information corresponding to the object of the target type. The preset feature information is feature information obtained by analyzing and testing in advance a standard product of the object of the target type.

In the embodiment of the present application, after the feature information of the object under detection is obtained, the preset feature information of the object of the target type may be acquired. Then, the feature information of the object under detection may be matched with the preset feature information of the object of the target type, and the detection result of the object under detection is determined according to a result of the matching. For example, under a condition that the feature information of the object under detection matches the preset feature information of the object of the target type, it may be determined that the object under detection is the object of the target type, that is, the detection result of the object under detection is the object of the target type.

It is understood that an output detection result may be a specific object of a target type, or may be a specific authenticity result output based on whether the object under detection is the object of the target type. For example, under a condition that the object under detection is the object of the target type, the output detection result may be that the object under detection is an authentic product. Under a condition that the object under detection is not the object of the target type, the output detection result may be that the object under detection is a fake product.

In the detection method, apparatus and system of the embodiments according to the present application, the feature information of the object under detection is obtained according to the first track before the particle penetrates the object under detection and the second track after the particle penetrates the object under detection, wherein the object under detection is a metal product, and the detection result of the object under detection is determined according to the feature information and the preset feature information of the object of the target type. Accordingly, since the feature information of the object under detection is related to an internal structure of the product, the feature information of the object under detection can reflect the internal structure. Under a condition that authenticity of a product is detected, feature information of the product and feature information of an authentic product are analyzed to reflect whether an internal structure of the product satisfies an internal structure of the authentic product. Therefore, an authenticity detection is performed by analyzing the feature information of the object under detection, thereby improving the accuracy of the detection result. Furthermore, the authenticity detection is performed by analyzing the feature information of the object under detection rather than analyzing density of the object under detection, so that the detection of the object under detection may be achieved, and a false detection caused by similar density may be avoided, thereby further improving the accuracy of the detection result.

In some embodiments, under a condition that a track range of the particle penetrating the object under detection matches a preset track range in the preset feature information of the object of the target type, it is determined that the object under detection is the object of the target type. The preset feature information may include the preset track range of the object of the target type, and the preset track range may include at least one of a preset range of the scattering angle and a preset distribution of the scattering angle.

Under this condition, a specific implementation process of the step S340 may be: obtaining, based on the first track and the second track of the particle, the first track range of the particle penetrating the object under detection.

Under this condition, a specific implementation process of the step S350 may be: acquiring the preset track range in the preset feature information of the object of the target type; and determining, under a condition that the first track range matches the preset track range, that the object under detection is the object of the target type.

The first track range is a track range of the particle penetrating the object under detection, for example, the first track range may include at least one of a range of the scattering angle and a distribution of the scattering angle.

Specifically, after the first track and the second track of the particle are obtained, the first track and the second track may be processed (for example, may be calculated and analyzed) to obtain the first track range of the particle penetrating the object under detection. Then, the preset feature information of the object of the target type may be acquired, and the preset track range in the preset feature information may be extracted, and the preset track range may include the preset range of the scattering angle and the preset distribution of the scattering angle. Then, the first track range of the particle penetrating the object under detection may be matched with the preset track range in the preset feature information of the object of the target type, so as to determine whether the first track range belongs to the preset track range.

Under a condition that the first track range belongs to the preset track range, it may be considered that the first track range matches the preset track range, and under this condition, the object under detection may be determined as the object of the target type. Conversely, under a condition that the first track range does not belong to the preset track range, it may be considered that the first track range does not match the preset track range, and under this condition, it may be determined that the object under detection is not the object of the target type. Accordingly, under a condition that the first track range of the particle penetrating the object under detection matches the preset track range in the preset feature information of the object of the target type, it may be considered that the feature information of the object under detection matches feature information of the object of the target type, that is, an internal structure of the object under detection matches an internal structure of the authentic product, and it is determined that the object under detection is the object of the target type, thereby effectively improving the accuracy of the detection result.

In some embodiments, under a condition that a first force of the object under detection on the particle matches a preset force of the object of the target type on the particle, the object under detection may be determined as the object of the target type. The preset feature information may include a preset force of the object of the target type on the particle, the preset force includes at least one of a preset scattering force and a preset blocking force.

Under this condition, a specific implementation process of the step S340 may be: obtaining, based on the first track and the second track of the particle, the first force of the object under detection on the particle.

Under this condition, a specific implementation process of the step S350 may be: acquiring the preset force in preset feature information of the object of the target type; and determining, under a condition that the first force matches the preset force, that the object under detection is the object of the target type.

The first force is a force of the object under detection on the particle, for example, the first force may include at least one of the scattering force and the blocking force.

Specifically, after the first track and the second track of the particle are obtained, the first track and the second track may be processed (for example, may be calculated and analyzed) to obtain the first force of the object under detection on the particle. Then, the preset feature information of the object of the target type may be acquired, and the preset force in the preset feature information may be extracted, and the preset force may include at least one of the preset scattering force and the preset blocking force. Then, the first force of the object under detection on the particle may be matched with the preset force of the object of the target type on the particle.

Under a condition that the first force matches the preset force, the object under detection may be determined as the object of the target type. Conversely, under a condition that the first force does not match the preset force, it may be determined that the object under detection is not the object of the target type.

Figure 4:
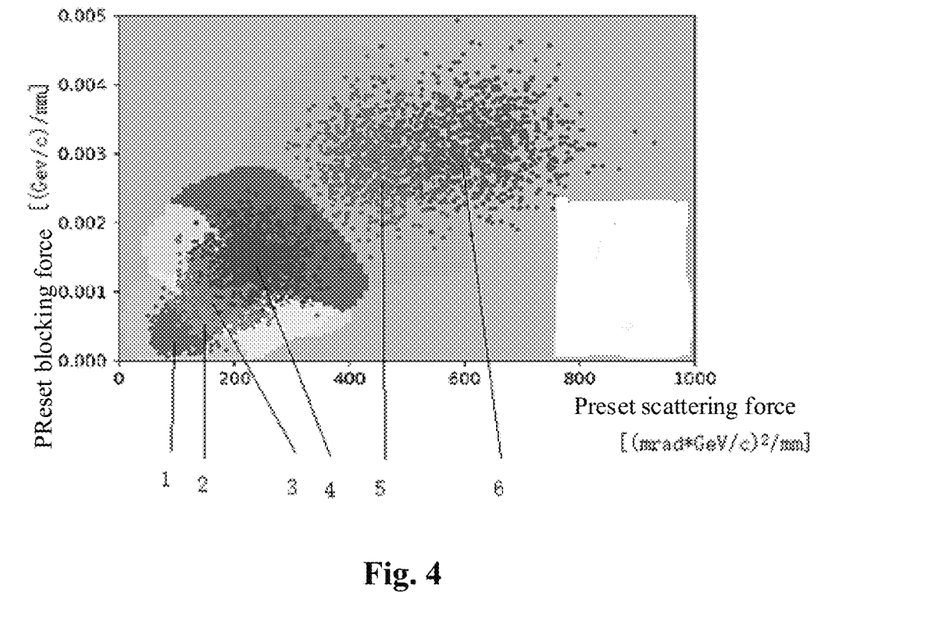
FIG. 4 is a schematic view of a distribution of a scattering force and a blocking force of an object of a target type on a muon.

FIG. 4 shows a schematic view of a distribution of a scattering force and a blocking force of an object of a target type on a muon. As shown in FIG. 4, 1 represents a scattering force and a blocking force of air on the muon, 2 represents a scattering force and a blocking force of paper on the muon, 3 represents a scattering force and a blocking force of a product made of morphine on the muon, 4 represents a scattering force and a blocking force of a product made of aluminum on the muon, 5 represents a scattering force and a blocking force of a product made of copper on the muon, and 6 represents a scattering force and a blocking force of a product made of lead on the muon. According to corresponding relationships between different objects of target types and scattering forces and blocking forces of the different objects of the target types on the muon, it may be determined that whether the object under detection is the object of the target type. Under a condition that a scattering force and a blocking force of the object under detection on the muon matches a scattering force and a blocking force of the object of the target type on the muon, the object under detection is determined as the object of the target type.

Accordingly, under a condition that the first force of the object under detection on the particle matches the preset force of the object of the target type on the particle, it may be considered that the feature information of the object under detection matches the feature information of the object of the target type, that is, the internal structure of the object under detection matches the internal structure of the authentic product, and therefore, it may be determined that the object under detection is the object of the target type, thereby improving the accuracy of the detection result.

The above is the detection system and the detection method according to the embodiments of the present application, and based on the detection system and the detection method, the embodiment of the present application further provides a detection apparatus which will be described in detail below.

Figure 5:
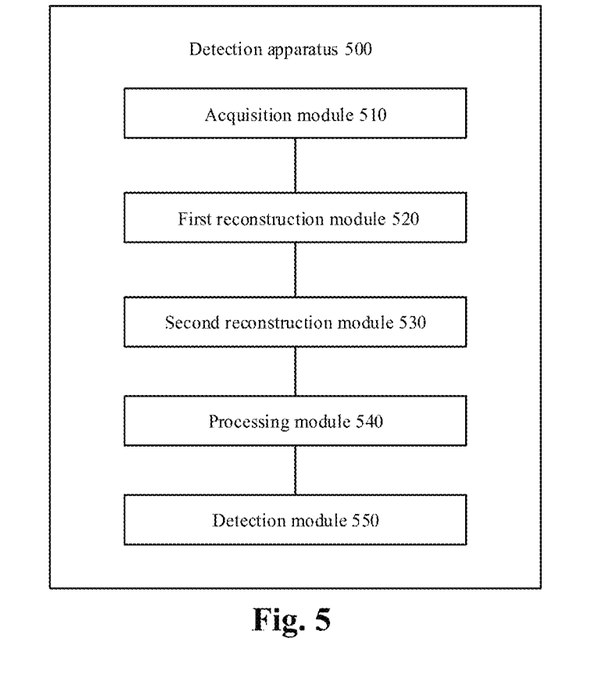
FIG. 5 is a schematic structural view of a detection apparatus according to an embodiment of the present application.

FIG. 5 is a schematic structural view of a detection apparatus according to an embodiment of the present application. As shown in FIG. 5, the detection apparatus 500 may include: an acquisition module 510, which may be configured to acquire information of at least two first positions through which a particle passes before penetrating an object under detection, and information of at least two second positions through which the particle passes after penetrating the object under detection, wherein the object under detection is a metal product; a first reconstruction module 520, which may be configured to reconstruct, based on the information of the at least two first positions, a first track before the particle penetrates the object under detection; a second reconstruction module 530, which may be configured to reconstruct, based on the information of the at least two second positions, a second track after the particle penetrates the object under detection; a processing module 540, which may be configured to process the first track and the second track to obtain feature information of the object under detection; and a detection module 550, which may be configured to determine, according to the feature information and preset feature information of an object of a target type, a detection result of the object under detection.

In the apparatus of the embodiment according to the present application, the feature information of the object under detection is obtained according to the first track before the particle penetrates the object under detection and the second track after the particle penetrates the object under detection, and the detection result of the object under detection is determined according to the feature information and the preset feature information of the object of the target type. Accordingly, since the feature information of the object under detection is related to the internal structure of the product, the feature information of the object under detection can reflect the internal structure. Under a condition that the authenticity of the product is detected, the feature information of the product and the feature information of the authentic product are analyzed to reflect whether the internal structure of the product satisfies the internal structure of the authentic product. Therefore, the authenticity detection is performed by analyzing the feature information of the object under detection, thereby improving the accuracy of the detection result. Furthermore, the authenticity detection is performed by analyzing the feature information of the object under detection rather than analyzing the density of the object under detection, so that the detection of the object under detection may be achieved, and the false detection caused by the similar density may be avoided, thereby further improving the accuracy of the detection result.

In some embodiments, the particle may include at least one of the muon and the electron.

In some embodiments, the preset feature information may include the preset track range of the object of the target type, and the preset track range may include at least one of the preset range of the scattering angle and the preset distribution of the scattering angle.

The processing module 540 may be configured to: obtain, based on the first track and the second track of the particle, a first track range of the particle penetrating the object under detection; The detection module 550 may specifically include: a first acquisition unit, which may be configured to acquire the preset track range in the preset feature information of the object of the target type; and a first determination unit, which may be configured to determine, under a condition that the first track range matches the preset track range, that the object under detection is the object of the target type.

Accordingly, under a condition that the first track range of the particle penetrating the object under detection matches the preset track range in the preset feature information of the object of the target type, it may be considered that the feature information of the object under detection matches the feature information of the authentic product, that is, the internal structure of the object under detection matches the internal structure of the authentic product, and under this condition, it is determined that the object under detection is the object of the target type, thereby further improving the accuracy of the detection result.

In some embodiments, the preset feature information may include a preset force of the object of the target type on the particle, and the preset force may include at least one of a preset scattering force and a preset blocking force.

The processing module 540 may be configured to: obtain, based on the first track and the second track of the particle, a first force of the object under detection on the particle;

The detection module 550 may specifically include: a second acquisition unit, which may be configured to acquire the preset force in the preset feature information of the object of the target type; and a second determination unit, which may be configured to determine, under a condition that the first force matches the preset force, that the object under detection is the object of the target type.

Accordingly, under a condition that the first force of the object under detection on the particle matches the preset force of the object of the target type on the particle, it may be considered that the feature information of the object under detection matches the feature information of the authentic product, that is, the internal structure of the object under detection matches the internal structure of the authentic product, and under this condition, it is determined that the object under detection is the object of the target type, thereby further improving the accuracy of the detection result.

It should be noted that, the present application is not limited to the specific configuration and processing described above and shown in the drawings. For the sake of brevity, a detailed description of the known method is omitted here. In the above embodiments, several specific steps are described and shown as examples. However, the method process of the present application is not limited to the specific steps described and shown, and those skilled in the art can make various changes, modifications and additions, or change the sequence of steps after comprehending the gist of the present application.

The functional blocks shown in the structural block diagrams above can be implemented as hardware, software, firmware, or a combination thereof. When implemented as hardware, it can be, for example, an electronic circuit, an application specific integrated circuit (ASIC), suitable firmware, a plug-in, a functional card, and the like. When implemented as software, elements of the present application are programs or code segments used to perform required tasks. The programs or code segments can be stored in a machine-readable medium, or transmitted on a transmission medium or a communication link through a data signal carried in a carrier wave. A "machine-readable medium" can include any medium that can store or transmit information. An example of the machine-readable media includes an electronic circuit, a semiconductor memory device, a Read-Only Memory (ROM), a flash memory, an erasable ROM (EROM), a floppy disk, a CD-ROM, an optical disk, a hard disk, a fiber optic medium, a radio frequency (RF) link, and the like. The code segments can be downloaded via a computer network such as the Internet, intranet, and the like.

It should also be noted that, according to the exemplary embodiments described in the present application, some methods or systems are described based on a series of steps or apparatuses. However, the present application is not limited to the above order of the steps, that is, the steps can be executed in the order described in the embodiments or in orders different from that in the embodiments, or several steps can be executed at the same time.

Aspects of the present disclosure are described above with reference to flowchart illustrations and/or block diagrams of methods, apparatuses and systems according to the embodiments of the present application. It should be understood that the each block of flowchart illustrations and/or the block diagrams, and a combination of various blocks of the flowchart illustrations and/or the block diagrams can be implemented by the computer program instructions. These computer program instructions can be provided to a processor of a general purpose computer, special purpose computer, or other programmable data processing apparatuses to produce a machine such that execution of the instructions via the processor of the computer or other programmable data processing apparatuses enables the implementation of the functions/actions specified in one or more blocks of the flowchart illustrations and/or block diagrams. Such processor can be but is not limited to a general purpose processor, a special purpose processor, an application specific processor, or a field programmable logic circuit. It should also be understood that each block of the block diagrams and/or the flowchart illustrations, and the combination of blocks of the block diagrams and/or the flowchart illustrations can also be implemented by special purpose hardware that performs specified functions or actions, or by the combination of the special purpose hardware and computer instructions.

The above are only specific implementations of the present application, those skilled in the art can clearly understand that the specific working processes of the above systems, modules and units can be referred to the corresponding processes in the foregoing method embodiments, which is not repeated here for the convenience and brevity of the description. It should be understood that the protection scope of the present application is not limited to this, and any person skilled in the art can easily think of various equivalent modifications or replacements within the technical scope disclosed in the present application, and these modifications or replacements should all be covered within the scope of protection of the present application.

What is claimed is:

1. A detection method, comprising:
acquiring information of at least two first positions through which a particle passes before penetrating an object under detection, and information of at least two second positions through which the particle passes after penetrating the object under detection, wherein the object under detection is a metal product;
reconstructing, based on the information of the at least two first positions, a first track before the particle penetrates the object under detection;
reconstructing, based on the information of the at least two second positions, a second track after the particle penetrates the object under detection;
processing the first track and the second track to obtain feature information of the object under detection; and
determining, according to the feature information and preset feature information of an object of a target type, a detection result of the object under detection,
wherein the preset feature information comprises a preset track range of the object of the target type or a preset force of the object of the target type on the particle, the preset track range comprises at least one of a preset range of a scattering angle and a preset distribution of the scattering angle, and the preset force comprises at least one of a preset scattering force and a preset blocking force;
processing the first track and the second track to obtain feature information of the object under detection comprises: obtaining, based on the first track and the second track of the particle, a first track range of the particle penetrating the object under detection or a first force of the object under detection on the particle;
determining, according to the feature information and the preset feature information of the object of the target type, the detection result of the object under detection comprises:
acquiring the preset track range or the preset force in the preset feature information of the object of the target type; and determining, under a condition that the first track range matches the preset track range or under a condition that the first force matches the preset force, that the object under detection is the object of the target type.

2. The detection method according to claim 1, wherein the particle comprises at least one of a muon and an electron.

3. A detection system, comprising:
a first detector, configured to detect information of at least two first positions through which a particle passes before penetrating an object under detection;
a second detector, configured to detect information of at least two second positions through which the particle passes after penetrating the object under detection;
a carrying unit, configured to carry the object under detection; and
a detection unit, configured to perform the method according to claim 1.

4. The detection system according to claim 3, wherein the first detector is arranged at one side of the carrying unit, and the first detector comprises at least two detectors; and
the second detector is arranged at the other side of the carrying unit, and the second detector comprises at least two detectors.

5. The detection system according to claim 3, wherein the particle comprises at least one of a muon and an electron.

6. The detection system according to claim 4, wherein the detectors comprise at least one of a drift tube, a scintillation crystal bar, and a position sensitive detector.

7. The detection system according to claim 3, wherein the carrying unit comprises at least one of a tray or a conveyor.

8. A detection apparatus, comprising:
an acquisition module, configured to acquire information of at least two first positions through which a particle passes before penetrating an object under detection, and information of at least two second positions through which the particle passes after penetrating the object under detection, wherein the object under detection is a metal product;
a first reconstruction module, configured to reconstruct, based on the information of the at least two first positions, a first track before the particle penetrates the object under detection;
a second reconstruction module, configured to reconstruct, based on the information of the at least two second positions, a second track after the particle penetrates the object under detection;
a processing module, configured to process the first track and the second track to obtain feature information of the object under detection; and
a detection module, configured to determine, according to the feature information and preset feature information of an object of a target type, a detection result of the object under detection,
wherein the preset feature information comprises a preset track range of the object of the target type or a preset force of the object of the target type on the particle, the preset track range comprises at least one of a preset range of a scattering angle and a preset distribution of the scattering angle, and the preset force comprises at least one of a preset scattering force and a preset blocking force;
the processing module is configured to obtain, based on the first track and the second track of the particle, a first track range of the particle penetrating the object under detection or a first force of the object under detection on the particle;
the detection module comprises:
a first acquisition unit, configured to acquire the preset track range or the preset force in the preset feature information of the object of the target type; and
a first determination unit, configured to determine, under a condition that the first track range matches the preset track range or under a condition that the first force matches the preset force, that the object under detection is the object of the target type.

9. The detection apparatus according to claim 8, wherein the particle comprises at least one of a muon and an electron.

* * * * *